(12) United States Patent
Tam

(10) Patent No.: US 6,518,253 B1
(45) Date of Patent: *Feb. 11, 2003

(54) TREATMENT OF VIRAL INFECTIONS USING THE L-ISOMER OF RIBAVIRIN

(76) Inventor: Robert Tam, ICN Pharmaceuticals, Inc., 3300 Hyland Ave., Costa Mesa, CA (US) 92626

(*) Notice: Subject to any disclaimer, the term of this patent is extended or adjusted under 35 U.S.C. 154(b) by 0 days.

This patent is subject to a terminal disclaimer.

(21) Appl. No.: 09/471,513

(22) Filed: Dec. 23, 1999

Related U.S. Application Data

(60) Provisional application No. 60/164,366, filed on Nov. 19, 1999, and provisional application No. 60/164,365, filed on Nov. 19, 1999.

(51) Int. Cl.⁷ .................. A61K 31/70; A01N 43/04
(52) U.S. Cl. ....................... 514/42; 514/23; 514/42; 514/43; 536/28.6; 536/28.7
(58) Field of Search .................... 514/23, 42, 43; 536/28.6, 28.7

(56) References Cited

U.S. PATENT DOCUMENTS 5,767,097 A * 6/1998 Tam ............................ 514/43
6,130,326 A * 10/2000 Ramasamy et al. ........... 514/43
6,150,337 A * 11/2000 Tam et al.

OTHER PUBLICATIONS

Yong–Lian Zhu, et al. *Anti–Hepatitis B Virus Activity and Metabolism of 2′,3′–Dideoxy–2′,3′–Didehydro –βL (–)–5–Fluoro–cytidine* Antimicrobial Agents and Chemotherapy 1998, 42(7):1805–1810.

* cited by examiner

Primary Examiner—James O. Wilson
Assistant Examiner—Traviss C. McIntosh
(74) Attorney, Agent, or Firm—Rutan & Tucker, LLP; Robert D. Fish

(57) ABSTRACT

A 1-(β-L-ribofuranosyl)-1,2,4-triazole-3-carboxamide is administered in a method of treatment of a viral infection in a patient, including HIV infection, HCV infection, or BHV infection.

12 Claims, 4 Drawing Sheets

TREATMENT OF VIRAL INFECTIONS USING THE L-ISOMER OF RIBAVIRIN

This application claims the benefit of U.S. provisional applications Nos. 60/164,366 and 60/164,365, both of which were filed Nov. 19, 1999, and both of which are incorporated herein by reference in their entirety.

FIELD OF THE INVENTION

The field of the invention is treatment of viral infections.

BACKGROUND OF THE BACKGROUND

Many viral infections are associated with a shift in the cytokine profile from a TH1 response to Th2 response, and recent research suggests that a control over the balance between the TH1 response and the Th2 response might be advantageous in terms of generation and/or maintenance of immunity against viral infection. An increased TH1 response appears to be especially important in HIV infection, where long-term survivors exhibit a TH1 dominated response, while progressors have a more Th2 dominated response. For example, Barker et al. suggest that disease progression in HIV results from a shift in cytokine production within the infected host from a TH1 to a Th2 pattern [Barker E, Mackewicz C E, Levy J A *Proc Natl Acad Sci USA* 1995 November 21;92(24):11135–9]. Similarly, a decrease in the Th2 response appears to be of therapeutic significance, since Reiser et al. report that Th2 cytokine levels are elevated in chronic hepatitis C virus infection [Reiser, M. et al.; *J Hepatol* 1997 March;26(3):471–8]. Various methods of influencing the TH1/Th2 balance are known, and may broadly be categorized in cytokine-related methods and non-cytokine related methods.

In cytokine related methods of treatment, cytokines are administered to modulate the TH1/Th2 balance towards either a TH1-type response or a Th2-type response. For example, Knight et al. postulate that treatment with IL-12 (Interleukine-12), a cytokine that promotes the development of TH1 cells, may be used as a treatment for AIDS since IL-12 administration has been shown to be effective at restoring cell-mediated immunity in mice infected with mouse AIDS virus or with Rauscher Leukemia Virus (RLV) [Knight, S. C. and Patterson, S., *Annu. Rev. Immunol.* 1994. 15: 593–615]. In another example, Gracie, J A. et al., demonstrated that administration of IL-18 to mice exhibited pleiotropic activities critical to the development of TH1 responses. [Gracie et al. *J Clin Invest* 1999 November 15;104(10):1393–1401]. Although the administration of cytokines typically results in relatively specific increases in desired TH1 cytokines, prolonged administration of cytokines may be problematic for various reasons. For example, the production of recombinant cytokines is relatively expensive, and isolation of non-recombinant cytokines from natural sources is generally difficult due to the very low concentration of cytokines in natural sources. A further problem is that cytokine preparations typically need to have a very high degree of purity in order to avoid allergic reactions upon repeated administration. Moreover, depending on the nature of the cytokine, cytokines may not be well tolerated in patients.

In a non-cytokine related method, immuno-modulatory substances other than cytokines are employed to modulate the balance between a TH1 response and a Th2 response. For example, Sprietsma J. E. suggests [Sprietsma J. E; *Med Hypotheses* 1999 July;53(1):6–16] that zinc ions ($Zn^{++}$) and nitric oxide (NO), together with glutathione (GSH) and its oxidized form, GSSG, may help to regulate an immune response to antigens. The author reports in more detail that deficiencies of $Zn^{++}$, NO and/or GSH shift the TH1/Th2 balance towards Th2, and that replenishment with $Zn^{++}$, NO and/or GSH may shift the TH1/Th2 balance towards TH1. Administration of $Zn^{++}$ or GSH/GSSG is especially advantageous, since these substances are non-toxic at even elevated concentrations, and inexpensive to produce. Furthermore, $Zn^{++}$ and GSH/GSSG preparations may be orally administered, and therefore significantly reduce the risk of allergic reactions, especially when the preparations are not ultrapure. However, the administration of $Zn^{++}$ and/or GSH/GSSG seems to be beneficial only to restore a Th1/Th2 balance from a Th2 dominated state, whereas it is unclear if administration of $Zn^{++}$ and/or GSH/GSSG may increase a TH1 response from a normal TH1/Th2 balance.

In another example, U.S. Pat. No. 6,150,337 incorporated herein by reference, a method is described in which the inventors employ the nucleoside analog Ribavirin (1-(5-Deoxy-β-D-ribo-furanosyl)-1,2,4-triazole-3-carboxamide) to modulate the balance of the TH1/Th2 response. The use of Ribavirin is especially advantageous for the treatment of viral infections, because Ribavirin not only modulates the immune response towards a TH1 response, but also acts as an inhibitory agent for viral replication. For example, Ribavirin has been successfully used in the treatment of Hepatitis C. Some of this effect has been attributed to antiviral effects and some of this effect has been attributed to the cytokine balance.

Although Ribavirin showed a desirable effect in virus count and immune status, prolonged administration of Ribavirin at relatively high doses was frequently associated with several side effects, including leukopenia and hemolytic anemia. In order to reduce the occurrence or severity of side effects, co-administration of Ribavirin with IFNα-2B has been introduced [Reichert, O., et al.1998; *Lancet* 351:83–87]. However, the co-administration of Ribavirin with IFNα-2B increases the cost of treatment significantly. Moreover, prolonged administration of IFNα-2B increases the risk of new side effects attributable to IFNα-2B.

Despite the relatively successful administration of Ribavirin in the treatment of viral diseases, the use of Ribavirin remains problematic due to the generation of various side effects. Therefore, there is a need to provide improved methods and compositions to modulate the TH1/Th2 balance at a relatively low or no toxic side effects for treatment of viral infections.

SUMMARY OF THE INVENTION

The present invention is directed to a method of treatment of a viral infection in a patient, in which Levovirin™ (1-(β-L-ribofuranosyl)-1,2,4-triazole-3-carboxamide) is administered to the patient, and wherein the viral infection is an HIV infection, a HCV infection, or a HBV infection.

In one aspect of the inventive subject matter, the administration of the Levovirin™ increases the TH1 response relative to the Th2 response in the patient, and it is especially contemplated that the TH1 response increases on an absolute. In further aspects of the inventive subject matter, Levovirin™ is administered in vivo, preferably injected i.v., or orally taken, wherein the preferred dose of Levovirin™ is between 0.1 mg/kg and 1.0 mg/kg.

Various objects, features, aspects and advantages of the present invention will become more apparent from the following detailed description of preferred embodiments of the invention, along with the accompanying drawings in which like numerals represent like components.

DETAILED DESCRIPTION

Figure 1:
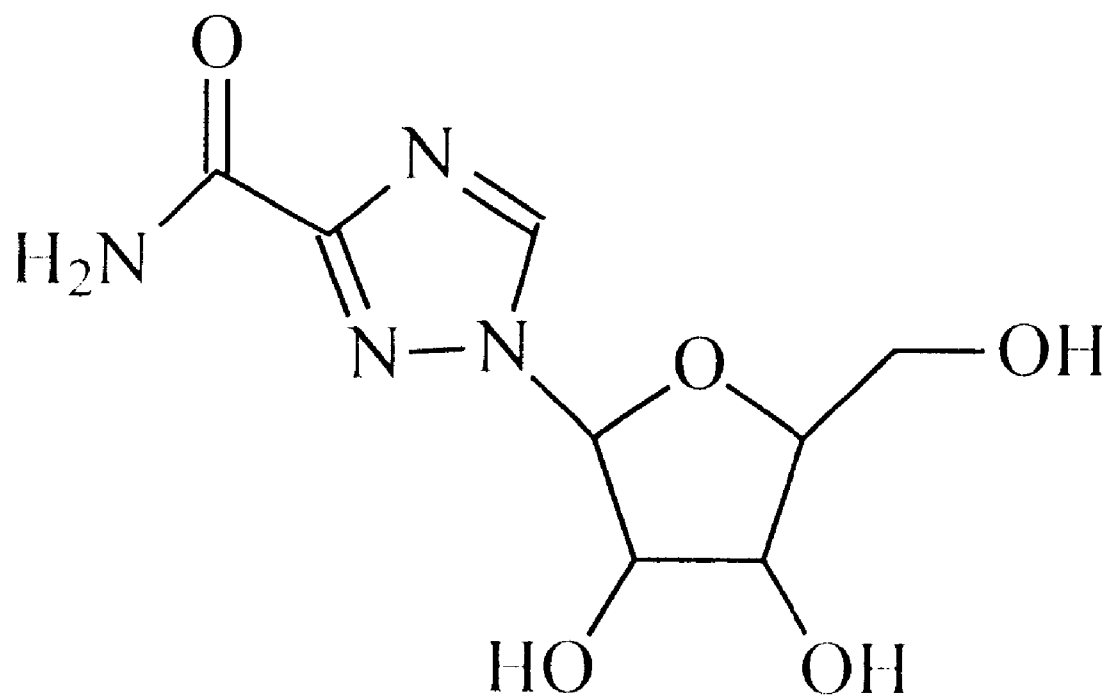
FIG. 1 is a structure of Levovirin™.
Figure 2:
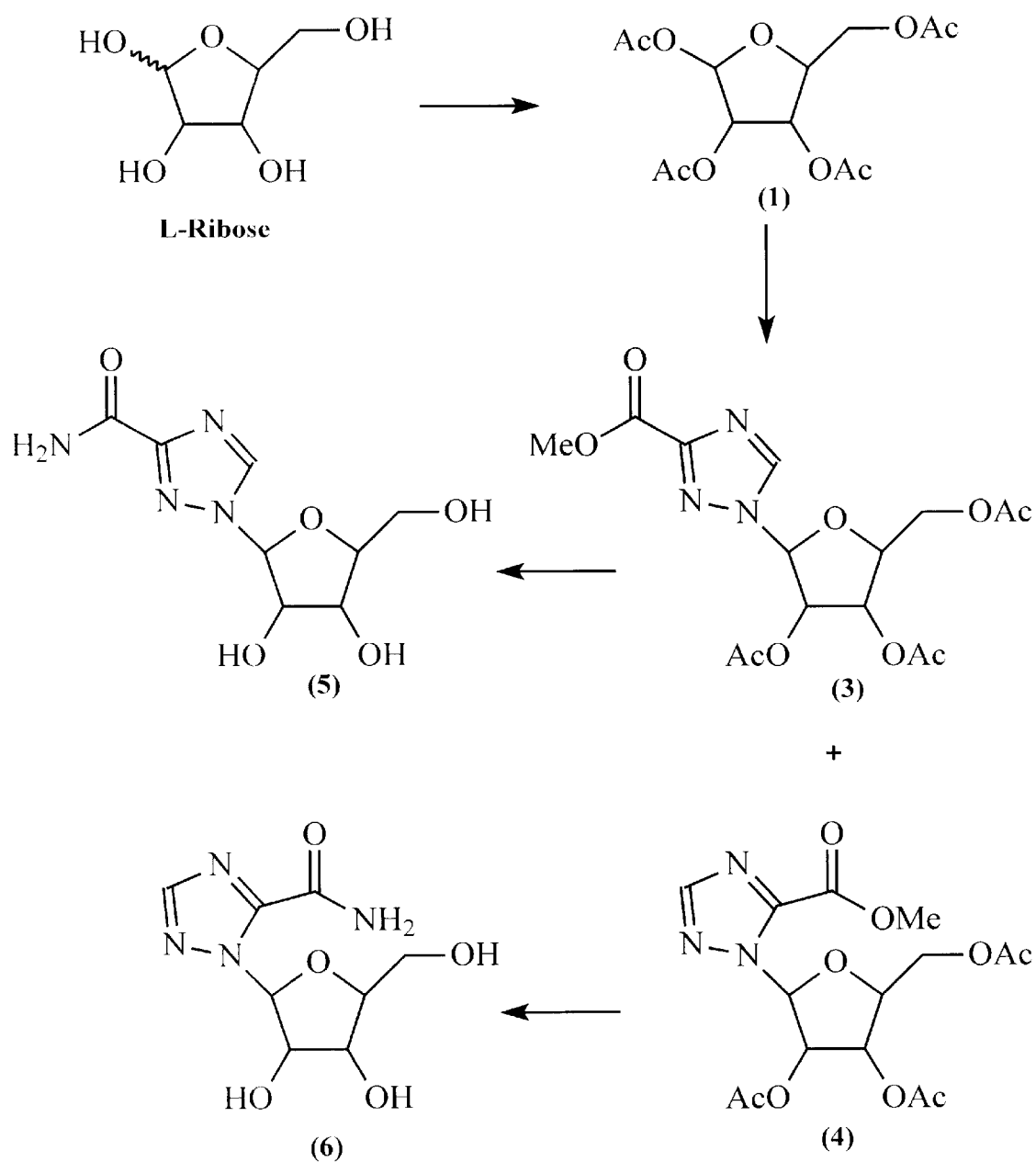
FIG. 2 is a synthetic scheme for the synthesis of Levovirin™.

As used herein, the term "viral infection" refers to any stage of a viral infection, including incubation phase, latent or dormant phase, acute phase, and development and maintenance of immunity towards a virus. Consequently, the term "treatment' is meant to include aspects of generating or restoring immunity of the patient's immune system, as well as aspects of suppressing or inhibiting viral replication.

As also used herein, lymphokines are a subset of cytokines produced by helper T cells, and are generally considered to fall into two subclasses, TH1 and Th2. TH1 cells (more modernly known as Type 1 cells) produce interleukin 2 (IL-2), tumor necrosis factor (TNFα) and interferon gamma (IFNγ), and are responsible primarily for cell-mediated immunity such as delayed type hypersensitivity and antiviral immunity. In contrast, Th2 cells (more modernly known as Type 2 cells) produce interleukins, IL4, IL-5, IL-6, IL-9, IL-10 and IL-13, and are primarily involved in assisting humoral immune responses such as those seen in response to allergens, e.g. IgE and IgG4 antibody isotype switching (Mosmann, 1989, *Annu Rev Immunol*, 7:145–173).

As further used herein, the terms TH1 and Th2 "responses" are meant to include the entire range of effects resulting from induction of TH1 and Th2 lymphocytes, respectively. Among other things, such responses include increased production of the corresponding cytokines, increased proliferation of the corresponding lymphocytes, and other effects associated with increased production of cytokines, including motility effects. A TH1 response is generally characterized by an increase in IL-2, TNF-α, and IFN-γ, whereas a Th2 response is typically characterized by an increase in IL4, IL-5, IL-6, and IL-10.

In a preferred embodiment, an HIV infected patient with a CD4 lymphocyte count of about 500 cells per microliter receives once daily over a period of 30 days a single injection of an aqueous solution of Levovirin™ in a total dose of 0.5 mg/kg body weight.

In alternative aspects of the inventive subject matter, the HIV infection need not be limited to a CD4 lymphocyte count of about 500 cells per microliter, but may also include lower CD4 lymphocyte counts, including CD4 lymphocyte counts between 500 and 300, 300–150, and less than 150. Similarly, higher CD4 lymphocyte counts (i.e. >500) are also contemplated. It should further be appreciated that various clinical markers other than virus titer and CD4 lymphocyte count may be appropriate, including direct and indirect assays for the presence of the HIV virus. For example, direct assays are quantitative culture of PBMCs and plasma HIV, qualitative and quantitative PCR methods and so forth. Indirect assays include qualitative and quantitative ELISA methods, etc.

With respect to the virus type of the viral infection it is contemplated that the treatment of the viral infection is not limited to a specific type or subtype of HIV virus, and it should be appreciated that various viruses other than a HIV are also contemplated. It is generally contemplated that alternative virus infections include virus infections that can be treated with Ribvirin, which is the D-isomer of Levovirin™. Especially contemplated alternative viral infections include HCV infection, and HBV infection.

In further alternative aspects of the inventive subject matter, the administration of Levovirin™ need not be restricted to a single daily injection over a period of 30 days, but may include alternative frequencies and routes. For example, where relatively high amounts of Levovirin™ need to be delivered, two to four or more daily injections are contemplated. Similarly, where high plasma concentrations of Levovirin™ are desired over an extended period, a permanent delivery is contemplated. For example, a more permanent delivery may include the use of a continuous infusion, an osmotic pump, or a sustained release implant. It should further be appreciated that the delivery route is not limited to injections, but appropriate delivery may include oral delivery, transdermal delivery, intranasal delivery pulmonary delivery, etc. Consequently, the formulation of alternative Levovirin™ preparations may include tablets, syrups, gels, aerosols, and so forth. It is further contemplated that the administration of Levovirin™ may also be in vitro. For example, a predetermined quantity of whole blood or fractions of whole blood may be pre-incubated with Levovirin™ in vitro to either boost or generate an immune reaction towards an immunogenic challenge.

With respect to the dosage of Levovirin™, it is contemplated that various alternative dosages are also appropriate, including dosages between 0.5 mg/kg and 0.1 mg/kg and less, but also dosages between 0.5 and 1.0 mg/kg and more. In general, the appropriate dosage will depend on multiple parameters, including the type of virus infection, the stage of the virus infection, the desired plasma concentration of Levovirin™, the duration of the treatment, etc. For example, while treatment success may be achieved with some viral infections at relatively low plasma concentrations of Levovirin™, other viral infections may require relatively high dosages.

In still further alternative aspects of the inventive subject matter, Levovirin™ may be combined with additional pharmaceutically active substances to assist in the treatment of the viral infections. Contemplated additional pharmaceutically active substances include antiviral agents and immune modulator substances. For example, antiviral agents are protease inhibitors, or nucleotide and nucleoside analogs, and immune modulator substances may include cytokines.

Although not wishing to be bound to any particular theory, it is contemplated that the administration of Levovirin™ is correlated with an increase of the TH1 response relative to the Th2 response in a patient, and it is especially contemplated that the relative increase of the Th1 response to the Th2 response is due to an absolute increase in the TH1 response. The cytokine levels may thereby be increased individually or collectively. For example, it is contemplated that administration of Levovirin™ to activated human PBMCs may result in a mean peak increase of the IL-2 level of at least 70%(by weight) over an activated control level. Alternatively, it is contemplated that administration of Levovirin™ to activated human PBMCs may result in a mean peak increase of the IFN-γ level of at least 20% (by weight) over an activated control level, or in a mean peak increase of the TNF-α level of at least 50% (by weight) over an activated control level (see also FIGS. 3A–C). In another example, it is contemplated that the increase in the TH1 response may comprises a mean peak increase over an activated control level in IL-2, IFN-γ, and TNF-α of 42% (by weight), 125% (by weight), and 72% (by weight), respectively.

It should especially be appreciated that while the spectrum of treatable viral infections is somewhat overlapping between Ribavirin and Levovirin™, Levovirin™ has a substantially reduced toxicity. For example, while oral administration of Ribavirin in rats at 180 mg/kg over four weeks produced significant hemolytic anemia and leukopenia, Levovirin™ did not produce any observable clinical pathology. Furthermore, it is especially contemplated that treatment of a viral disease with Levovirin™ is predominantly based on the modulation of the TH1/Th2 balance towards a Th1 dominated response, and not predominantly based an a direct antiviral effect. The term "direct antiviral" effect or activity as used herein refers to an immediate effect or activity of a drug on viral assembly or replication. In contrast, a reduction of viral activity or replication that is at least in part mediated by one or more components of the immune system is not considered a "direct antiviral" effect or activity. Likewise, it should be appreciated that a relative reduction of the Th2 response during a treatment according to the inventive subject matter may be especially advantageous in diseases that are correlated with an increased Th2 response (e.g., HCV infection).

EXAMPLES

The following examples illustrate an exemplary synthesis and various applications of Levovirin™.

Example 1

Synthesis of Levovirin™

1,2,3,5-Tetra-O-acetyl-β-L-ribofuranose (1): To a stirred solution of L-ribose (50.0 g, 333.33 mmol) in anhydrous methanol (500 ml) at room temperature was added freshly prepared dry methanolic HCl (40 ml, prepared by bubbling dry HCl gas into methanol at 0° C. to a weight increase of 4 g) via syringe during 15 min period under argon atmosphere. After the addition of methanolic HCL, the reaction mixture was allowed to stir at room temperature for 3–4 h. Dry pyridine (100 ml) was added and evaporated to dryness under high vacuum below 40° C. This process was repeated a second time with additional dry pyridine (100 ml). The residue was dissolved in dry pyridine (250 ml) and cooled in an ice bath to 0° C. under argon atmosphere. To this cold stirred solution was added acetic anhydride (100 ml) via a dropping funnel during 15 min period. After the addition of acetic anhydride, the reaction was allowed to stir at room temperature under exclusion of moisture for 24 h. The reaction mixture was evaporated to dryness. The residue was partitioned between ethyl acetate (400 ml) and water (400 ml), and extracted in EtOAc. The aqueous layer was extracted again with EtOAc (100 ml). The combined EtOAc extract was washed with water (400 ml), saturated NaHCO₃ (2×300 ml), water (300 ml) and brine (200 ml). The organic extract was dried over anhydrous Na₂SO₄, filtered and the filtrate evaporated to dryness. The residue was co-evaporated with dry toluene (2×150 ml) at high vacuum. The dried oily residue (92 g, 95%) was used as such for the following reaction without further characterization.

The syrup (92 g) from the above reaction was dissolved in glacial acetic acid (300 ml) and treated with acetic anhydride (75 ml) at room temperature. The solution was cooled to 0–5° C. in an ice bath under argon atmosphere. Concentrated H₂SO₄ (21 ml) was added slowly during a 15 min period. After the addition of H₂SO₄, the reaction mixture was stirred at room temperature for 14 h and poured on crushed ice (500 g), and stirred until the ice melts. Water (500 ml) was added and extracted with CHCl₃ (2×300 ml). The chloroform extract was washed with water (3×400 ml), saturated NaHCO₃, (2×300 ml), water (200 ml) and brine (200 ml). The washed organic extract was dried over anhydrous MgSO₄, filtered and evaporated to dryness to give an oily residue (99 g). The residue was co-evaporated with dry toluene (200 ml) and dissolved in ethyl ether (200 ml) which upon cooling at 10° C. for a day produced colorless crystals. The crystalline solid was filtered, washed with hexanes:ether (2:1, 50 ml) and dried to give 60.5 g product.

Methyl-1-(2,3,5-tri-O-acetyl-β-L-ribofuranosyl)-1,2,4-triazole-3-carboxylate (3) and Methyl-1-(2,3,5-tri-O-acetyl-β-L-ribofuranosyl)-1,2,4-triazole-5-carboxylate (4): A mixture of methyl-1,2,4-triazole-3-carboxylate (25.4 g, 200 mmol), 1,2,3,5-tetra-O-acetyl-β-L-ribofuranose (63,66 g, 200 mmol) and bis(p-nitrophenyl)phosphate (1 g) were placed in a RB-flask (500 ml). The flask was placed in a preheated oil bath at 165–175° C. under water aspirator vacuum with stirring for 25 min. The acetic acid displaced was collected in an ice-cold trap that is placed between the aspirator and the RB flask. The flask was removed from the oil bath and allowed to cool. When the temperature of the flask reached roughly 60–70° C., EtOAc (300 ml) and saturated NaHCO₃ (150 ml) were introduced, and extracted in EtOAc. The aqueous layer was extracted again with EtOAc (200 ml). The combined EtOAC extract was washed with saturated NaHCO₃ (300 ml), water (300 ml) and brine (200 ml). The organic extract was dried over anhydrous Na₂SO₄, filtered and the filtrate was evaporated to dryness. The residue was dissolved in EtOH (100 ml) and diluted with MeOH (60 ml), which on cooling at 0° C. for 12 h produced colorless crystals. The solid was filtered, washed with minimum cold EtOH (20 ml) and dried at high vacuum over solid NaOH to give 60 g (78%). The filtrate was evaporated to dryness and purified on silica column using ChCl₃→EtOAc (9:1) as the eluent. Two products were isolated from the filtrate: fast moving product 8.5 g (11%) and slow moving product 5 g(6.5%). The slow moving product matched with the crystallized product. The fast moving product was found to be (4) and obtained as foam. The combined yield of (3) was 65 g (84%).

1-β-Ribofuranosyl-1,2,4-triazole-3-carboamide (5): Methyl-1-(2,3,5-tri-O-acetyl-β-L-ribofuranosyl)-1,2,4-triazole-3-carboxylate (62 g, 161 mmol) was placed in a steel bomb and treated with freshly prepared methanolic ammonia (350 ml, prepared by passing dry HCL gas into dry methanol at 0° C. until saturation) at 0° C. The steel bomb was closed and stirred at room temperature for 18 h. The steel bomb was then cooled to 0° C., opened and the content evaporated to dryness. The residue was treated with dry ethanol (100 ml) and evaporated to dryness. The residue obtained was triturated with acetone to give a solid, which was filtered and washed with acetone. The solid was dried overnight at room temperature and dissolved in a hot EtOH (600 ml) and water (10 ml) mixture. The volume of the EtOH solution was reduced to 150 ml by heating and stirring on a hot plate. The hot EtOH solution on cooling provided colorless crystals, which were filtered, washed with acetone and dried under vacuum. Further concentration of the filtrate gave additional material. The total yield was 35 g (89%).

Example 2

Determination of Cytokine Pattern in Response to Levovirin™ and Ribavirin

Figure 3A:
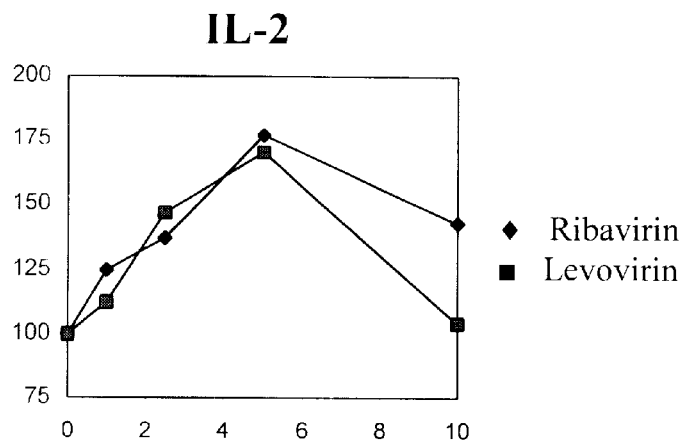
FIGS. 3A–C are graphs depicting various biological effects of Levovirin™ and Ribavirin on elements of the TH1 response.
Figure 3B:
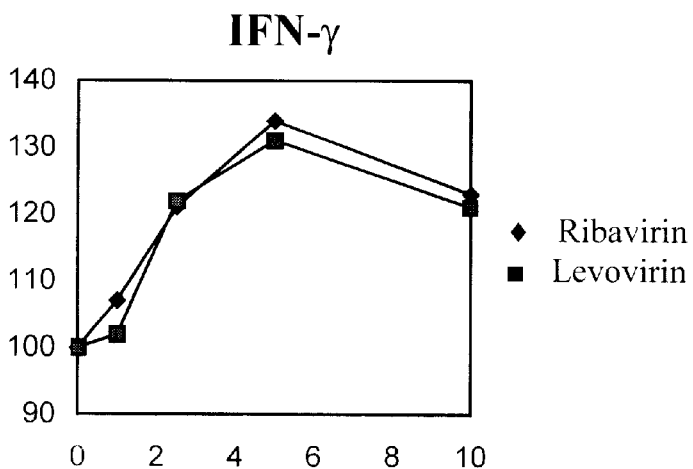
Figure 3C:
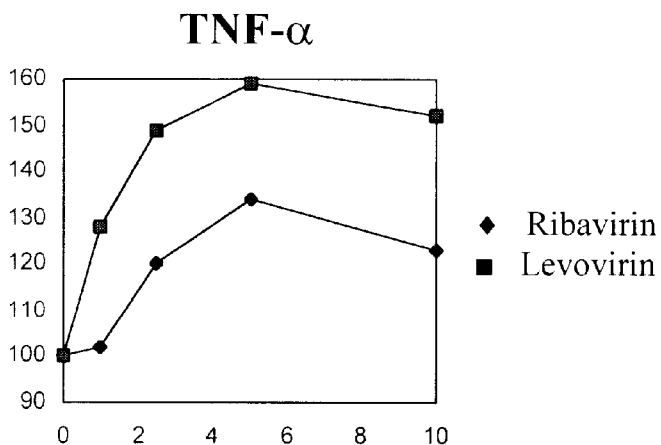

Peripheral blood mononuclear cells were isolated from healthy donors by density gradient centrifugation followed by T cell enrichment using Lymphokwik (One Lambda, Canoga Park, Calif.). Contaminating monocytes were removed by adherence to plastic. Purified T cells were >99%CD2$^+$, <1%HLA-DR$^+$, and <5% CD25$^+$, and were maintained in RPMI-AP5 (RPMI1640 medium containing 5% autologous plasma, 1% glutamine, 1% penicillin/streptomycin and 0.05% 2-mercaptoethanol). For the determination of cytokine protein levels, T-cells (0.2*10$^6$ in a volume of 0.2 ml) were activated by the addition of 80 ng of Staphylococcal enterotoxin B (SEB, Sigma, St. Louis, Mo.) and incubated in 96-well plates in the presence of 0–10 $\mu$M of Levovirin™ or Riboviron for 48 hrs at 37° C. Following activation, supernatants were analyzed for cell-derived cytokine production. The cytokine determination was performed using ELISA kits specific for IL-2, IFN-$\gamma$ and TNF-$\alpha$ (Biosource, Camarillo, Calif.). All ELISA results were expressed as pg/ml. Data shown as percentage of activated control, calculated as the ratio of activated T cell cytokines level in the presence of Levovirin™ or Ribavirin over the cytokine level of untreated activated T cells times 100%. Thus, a zero effect on cytokine levels would give a percentage of activated control value of 100%. FIGS. 3A–C show the similarity of dose responses between T cells treated with Ribavirin or Levovirin™ and various TH1 cytokines. Table 1 shows the effect of Ribavirin and Levovirin™ on SEB stimulated T cell expression of the TH1 cytokines IL-2, IFN-$\gamma$, and TNF-$\alpha$. The present data clearly suggest that Levovirin™ offers significant potential for the treatment of those diseases in which Type 1 cytokines play a critical role.

TABLE 1

| Treatment | IL-2 | IFN-$\gamma$ | TNF-$\alpha$ |
|---|---|---|---|
| SEB | 100 | 100 | 100 |
| SEB + Ribavirin | 143 ± 18 | 131 ± 6 | 124 ± 4 |
| SEB + Levovirin ™ | 131 ± 12 | 122 ± 3 | 144 ± 7 |

All data are shown collectively as mean percentage of activated control (+/- Standard deviation) for all cytokines. The absolute level (pg/ml +/- St. Dev.) of SEB induced Type 1 cytokine secretion was for IL-2 640 +/- 36, for IFN-$\gamma$ 462 +/- 37, and for TNF-$\alpha$ 223 +/- 27. Resting levels were <30 pg/ml for all cytokines.

Example 3

Direct Antiviral Activity and Cytotoxicity Assays

In vitro testing for direct antiviral activity of Levovirin™ and Ribavirin against influenza A and B, parainfluenza 1 and 2, and respiratory syncytial virus were performed as described in Huffinan, J. H. et al. *Antiviral Chem. and Chemother*. 1997, 8: 75–83 and Barnard, D. L. et al. *Antiviral Chem. and Chemother* 1997, 8: 223–233. Anti-human immunodeficiency virus activity was assessed by the National Cancer Institute using a procedure designed to detect agents acting at any stage of the virus reproductive cycle [Weislow, O. W. et al., *J. Natl. Cancer Inst.* 1989, 81: 577–586]. Anti-hepatitis B (HBV) activity was monitored by using an assay as described by Marion et al., *Hepatology* 1987, 7: 724–731. Anti-HIV activity and cytotoxicity for Ribavirin was determined from previous data [McCormick, J. B., *Lancet*, 1998, II: 1367–1369.

Table 2 shows a comparison of the direct antiviral activity and cytotoxicity of Levovirin™ and Ribavirin in cells infected with various viruses.

TABLE 2

| Compound | Activity | HBV | HIV | INFL.A | INFL.B | PARA 1 | PARA 3 | RSV |
|---|---|---|---|---|---|---|---|---|
| Levovirin ™ | Dir.Antiviral | >100 | >600 | >200 | >200 | >1000 | >1000 | >1000 |
|  | Cytotoxicity | >100 | >600 | >200 | >200 | >1000 | >1000 | >1000 |
| Ribavirin | Dir.Antiviral | >100 | 40 | 6.1 | 1.9 | 40 | 4 | 5 |
|  | Cytotoxicity | 53 | >40 | 56 | >100 | >1000 | 480 | 100 |

The viruses tested were Hepatitis B (HBV), human immunodeficiency virus (HIV), Influenza (INFL) A and B, Parainfluenza (PARA) 1 and 3, and respiratory syncytial virus (RSV). Antiviral activity (EC$_{50}$) or cytotoxicity (CC$_{50}$) are all shown in $\mu$M.

Example 4

Anti-inflammatory Activities of Levovirin™ in Concanavalin A Induced Hepatitis

Figure 4:
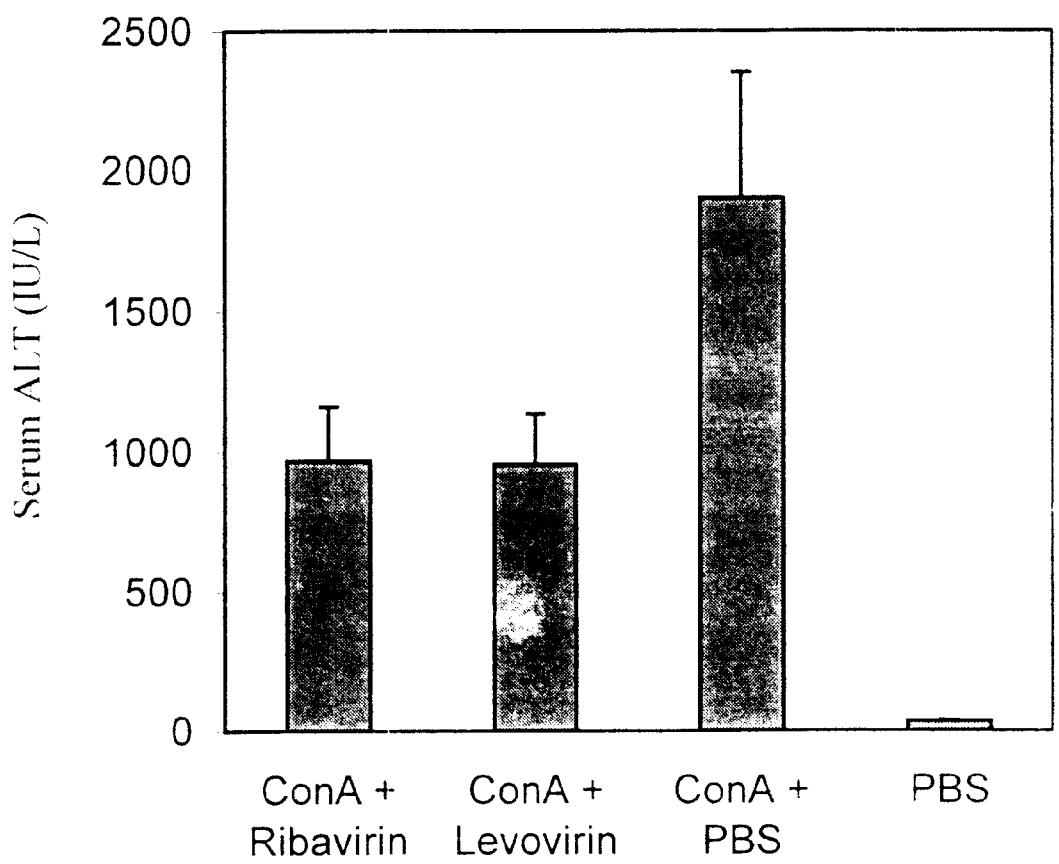
FIG. 4 is a graph showing serum ALT levels in Con A injected mice dependence of treatment with Levovirin™ and Ribavirin.

BALB/c mice (6 per group were injected intraperitoneally with a single dose of 20 $\mu$g (1 mg/kg) of Ribavirin or Levovirin™, or 200 $\mu$l PBS 1 hr prior to intravenous tail vein injection with 0.3 mg Concanavalin A (Con A, Calbiochem, San Diego, Calif.). After 24 hr the mice were anesthetized with Penthrane and exanguinated by cardiac puncture to obtain whole blood. Serum was obtained from clotted blood and used for determinations of serum alanine aminotransferase (ALT). Serum ALT levels were determined using an enzyme activity assay (Sigma) based on the colorimetric measurement of the products (pyruvic acid and glutamic acid) formed from the catalysis of the substrates, alanaine and $\alpha$-ketoglutaric acid. FIG. 4 shows the amounts of serum ALT in dependence of Ribavirin or Levovirin™, or PBS. Both Ribavirin and Levovirin™ were able to substantially reduce Con A induced serum ALT levels from about 1900 U/ml to 969 U/ml+/-192 for Ribavirin and 954 U/ml+/-179 for Levovirin™.

Thus, specific embodiments and applications of compounds and methods of treating a viral infection with Levovirin™ have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of treatment of a viral infection in a patient comprising:
   administering a compound according to structure 1; wherein structure 1 is

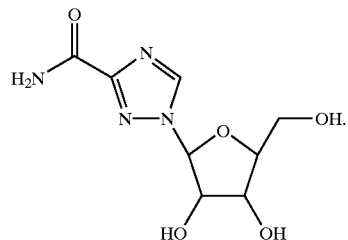

2. The method of claim 1 wherein the viral infection is selected from the group consisting of an HIV infection, an HCV infection, and an HBV infection.

3. The method of claim 1 wherein the step of administering a compound increases a Th1 response relative to a Th2 response in the patient.

4. The method of claim 3 wherein the Th1 response increases.

5. The method of claim 4 wherein the increase in the Th1 response comprises a mean peak increase over an activated control level in IL-2 of at least 70% (by weight).

6. The method of claim 4 wherein the increase in the Th1 response comprises a mean peak increase over an activated control level in IFN-γ of at least 20% (by weight).

7. The method of claim 4 wherein the increase in the Th1 response comprises a mean peak increase over an activated control level in TNF-α of at least 50% (by weight).

8. The method of claim 4 wherein the increase in the Th1 response comprises a mean peak increase over an activated control level in IL-2, IFN-γ, and TNF-α of 42% (by weight), 125% (by weight), and 72% (by weight), respectively.

9. The method of claim 1 wherein the step of administering a compound comprises in vivo administration.

10. The method of claim 1 wherein the step of administering a compound comprises oral administration.

11. The method of claim 1 wherein the step of administering a compound comprises injection.

12. The method of claim 1 wherein the step of administering a compound comprises administering the compound in a dose between 0.1 mg per kg of body weight of the patient and 1.0 mg per kg of body weight of the patient.

* * * * *